(12) United States Patent
Newswanger et al.

(10) Patent No.: US 11,320,783 B2
(45) Date of Patent: May 3, 2022

(54) FLEXIBLE TIP OPTICAL IMAGING

(71) Applicant: Open Water Internet Inc., San Francisco, CA (US)

(72) Inventors: Craig Newswanger, Oakland, CA (US); Mary Lou Jepsen, Sausalito, CA (US); Ian David O'Donnell, San Jose, CA (US)

(73) Assignee: Open Water Internet Inc., San Francisco, CA (US)

( * ) Notice: Subject to any disclaimer, the term of this patent is extended or adjusted under 35 U.S.C. 154(b) by 567 days.

(21) Appl. No.: 16/279,951

(22) Filed: Feb. 19, 2019

(65) Prior Publication Data

US 2020/0085309 A1     Mar. 19, 2020

Related U.S. Application Data

(60) Provisional application No. 62/731,308, filed on Sep. 14, 2018.

(51) Int. Cl.
*G03H 1/04* (2006.01)
*A61B 5/00* (2006.01)
(Continued)

(52) U.S. Cl.
CPC ......... *G03H 1/0443* (2013.01); *A61B 5/0051* (2013.01); *A61B 5/0066* (2013.01); *A61B 5/0097* (2013.01); *A61B 5/745* (2013.01); *A61B 8/463* (2013.01); *G03H 1/0465* (2013.01); *H04N 5/33* (2013.01); *A61B 2562/0238* (2013.01);
(Continued)

(58) Field of Classification Search
CPC ....... A61B 5/68; A61B 5/6801; A61B 5/6813; A61B 5/6814; A61B 5/0097; A61B 2562/0238; A61B 5/0042; A61B 5/0051; A61B 5/0066; A61B 5/745; A61B 8/463; G01S 15/8968; G03H 1/0443; G03H 1/0465; G03H 1/22; G03H 1/2202; G03H 2001/0083; G03H 2001/0088; G03H 2001/0447; G03H 2001/0452; G03H 2222/16; G03H 2223/16; G03H 2223/23;
(Continued)

(56) References Cited

U.S. PATENT DOCUMENTS 6,172,760 B1   1/2001  Son
6,956,650 B2   10/2005 Boas
(Continued)

OTHER PUBLICATIONS

Arridge et al. Nonuniqueness in diffusion-based optical tomography, Optics Letters, Jun. 1, 1998, vol. 23, No. 11, pp. 882-884.
(Continued)

*Primary Examiner* — Amelie R Davis
(74) *Attorney, Agent, or Firm* — Freestone Intellectual Property Law PLLC; Aaron J. Visbeek

(57) ABSTRACT

A system or device includes a member structure, a plurality of flexible members, and a plurality of tips disposed at ends of the flexible members. The member structure includes an ultrasonic emitter configured to emit an ultrasonic imaging signal. The plurality of flexible members are coupled to the member structure. The plurality of tips are disposed at ends of the flexible members. At least one tip of the plurality of tips includes an image sensor configured to receive an infrared exit signal.

20 Claims, 13 Drawing Sheets

(51) Int. Cl.
    *A61B 8/00*      (2006.01)
    *H04N 5/33*      (2006.01)

(52) U.S. Cl.
    CPC . *G03H 2001/0452* (2013.01); *G03H 2222/16* (2013.01); *G03H 2223/16* (2013.01); *G03H 2223/23* (2013.01); *G03H 2223/24* (2013.01); *G03H 2223/53* (2013.01)

(58) Field of Classification Search
    CPC ... G03H 2223/24; G03H 2223/53; H04N 5/33
    See application file for complete search history.

(56) References Cited

U.S. PATENT DOCUMENTS

| | | | |
|---|---|---|---|
| 7,119,906 | B2 | 10/2006 | Pepper |
| 7,460,248 | B2 | 12/2008 | Kurtz |
| 7,551,809 | B2 | 6/2009 | Taira |
| 7,610,082 | B2 | 10/2009 | Chance |
| 7,647,091 | B2 | 1/2010 | Ntziachristos |
| 7,728,986 | B2 | 6/2010 | Lasker |
| 7,804,070 | B1 | 9/2010 | Pan |
| 7,821,640 | B2 | 10/2010 | Koenig |
| 7,822,468 | B2 | 10/2010 | Stammes |
| 7,826,878 | B2 | 11/2010 | Alfano |
| 7,898,649 | B2 | 3/2011 | Masumura |
| 7,965,389 | B2 | 6/2011 | Da Silva |
| 7,983,740 | B2 | 7/2011 | Culver |
| 7,928,896 | B2 | 8/2011 | Jin |
| 8,014,847 | B2 | 9/2011 | Shastri |
| 8,120,784 | B2 | 2/2012 | Da Silva |
| 8,170,651 | B2 | 5/2012 | Lorenzo |
| 8,239,006 | B2 | 8/2012 | Zhu |
| 8,263,947 | B2 | 9/2012 | Da Silva |
| 8,289,502 | B2 | 10/2012 | Yoshida |
| 8,326,567 | B2 | 12/2012 | Masumura |
| 8,330,642 | B2 | 12/2012 | Jin |
| 8,355,131 | B2 | 1/2013 | Bakker |
| 8,357,915 | B2 | 1/2013 | Guyon |
| 8,374,409 | B2 | 2/2013 | Jochemsen |
| 8,416,421 | B2 | 4/2013 | Wang |
| 8,450,674 | B2 | 5/2013 | Yang |
| 8,451,450 | B2 | 5/2013 | Heng |
| 8,520,921 | B2 | 8/2013 | Ziegler |
| 8,525,998 | B2 | 9/2013 | Yaqoob |
| 8,527,242 | B2 | 9/2013 | Granot |
| 8,531,662 | B2 | 9/2013 | Van Der Mark |
| 8,563,932 | B2 | 10/2013 | Fang |
| 8,634,077 | B2 | 1/2014 | Hu |
| 8,649,015 | B2 | 2/2014 | Ichihara |
| 8,917,442 | B2 | 3/2014 | Baym |
| 8,717,574 | B2 | 5/2014 | Yang |
| 8,814,795 | B2 | 8/2014 | Derode |
| 8,817,255 | B2 | 8/2014 | Masumura |
| 8,830,573 | B2 | 9/2014 | Cui |
| 8,847,175 | B2 | 9/2014 | Laidevant |
| 8,937,284 | B2 | 1/2015 | Fang |
| 8,954,130 | B2 | 2/2015 | Masumura |
| 8,976,433 | B2 | 3/2015 | Masumura |
| 9,012,869 | B2 | 4/2015 | Andersson-Engels |
| 9,036,970 | B2 | 5/2015 | Guyon |
| 9,037,216 | B2 | 5/2015 | Hielscher |
| 9,057,695 | B2 | 6/2015 | Masumura |
| 9,131,851 | B2 | 9/2015 | Fukutani |
| 9,134,229 | B2 | 9/2015 | Lesage |
| 9,179,842 | B2 | 11/2015 | Nakaji |
| 9,207,171 | B2 | 12/2015 | Nadakuditi |
| 9,234,841 | B2 | 1/2016 | Wang |
| 9,282,932 | B2 | 3/2016 | Kudo |
| 9,297,752 | B2 | 3/2016 | Shimokawa |
| 9,304,490 | B2 | 4/2016 | Masumura |
| 9,313,423 | B2 | 4/2016 | Wang |
| 9,335,604 | B2 | 5/2016 | Popovich |
| 9,335,605 | B2 | 5/2016 | Wang |
| 9,341,569 | B2 | 5/2016 | 'T Hooft |
| 9,354,166 | B2 | 5/2016 | Judkewitz |
| 9,373,020 | B2 | 6/2016 | Kudo |
| 9,407,796 | B2 | 8/2016 | Dinten |
| 9,427,213 | B2 | 8/2016 | Suzuki |
| 9,480,425 | B2 | 11/2016 | Culver |
| 9,486,142 | B2 | 11/2016 | Hielscher |
| 9,488,574 | B2 | 11/2016 | Koehler |
| 9,509,956 | B2 | 11/2016 | Piestun |
| 9,622,663 | B2 | 4/2017 | Fang |
| 9,689,797 | B2 | 6/2017 | Sun |
| 9,724,489 | B2 | 8/2017 | Barbour |
| 9,730,649 | B1 | 8/2017 | Jepsen |
| 9,750,413 | B2 | 9/2017 | Sandusky |
| 2008/0312533 | A1* | 12/2008 | Balberg ............... A61B 8/0808 600/437 |
| 2010/0016732 | A1 | 1/2010 | Wells |
| 2012/0070817 | A1 | 3/2012 | Wang et al. |
| 2014/0081096 | A1 | 3/2014 | Baym |
| 2014/0114181 | A1 | 4/2014 | Wu |
| 2014/0303473 | A1 | 10/2014 | Nanaumi |
| 2015/0182121 | A1 | 7/2015 | Barbour |
| 2015/0238092 | A1 | 8/2015 | Masumura |
| 2015/0241342 | A1 | 8/2015 | Zhou |
| 2015/0282731 | A1* | 10/2015 | Hill .................... A61B 5/18 600/545 |
| 2015/0346027 | A1 | 12/2015 | Khare |
| 2015/0351635 | A1 | 12/2015 | Cerussi |
| 2016/0085135 | A1 | 3/2016 | Park |
| 2016/0157723 | A1 | 6/2016 | Kanick |
| 2016/0262723 | A1 | 9/2016 | Zhu |
| 2016/0363527 | A1 | 12/2016 | Ruan |
| 2017/0118423 | A1 | 4/2017 | Zhou |
| 2017/0163946 | A1 | 6/2017 | Komanduri |
| 2017/0168565 | A1 | 6/2017 | Cohen |
| 2017/0202633 | A1 | 7/2017 | Liu |
| 2017/0230555 | A1 | 8/2017 | Tabirian |
| 2017/0231501 | A1 | 8/2017 | Culver |

OTHER PUBLICATIONS

Hofmann et al. Differential light detector, Rev. Sci. Instrum, Feb. 1979, vol. 50, No. 2, pp. 249-252.

Freund et al. Memory Effects in Propagation of Ooptical Waves through Disordered Media, Physical Review Letters, Nov. 14, 1988, vol. 61, No. 20, pp. 2328-2331.

Goodman et al. Wavefront-Reconstruction Imaging Through Random Media, Jun. 15, 1966, vol. 8, No. 12, pp. 311-313.

Peng et al. Low loss liquid crystals for infrared applications, Liquid Crystal, 2014, vol. 41, No. 11, pp. 1545-1552.

* cited by examiner

FLEXIBLE TIP OPTICAL IMAGING

CROSS-REFERENCE TO RELATED APPLICATIONS

This application claims priority to U.S. provisional Application No. 62/731,308 filed Sep. 14, 2018, which is hereby incorporated by reference.

TECHNICAL FIELD

This application is related to optical imaging and in particular to optical imaging with flexible tips.

BACKGROUND INFORMATION

Imaging devices are used in contexts such as healthcare, navigation, and security, among others. Imaging systems often measure radio waves or light waves to facilitate imaging. Imaging that measures light scattered by an object is especially challenging. Advances to the devices, systems, and methods of optical imaging are sought to providing access for imaging components that also improve the form factor, increase comfort, or improve accuracy.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1A:
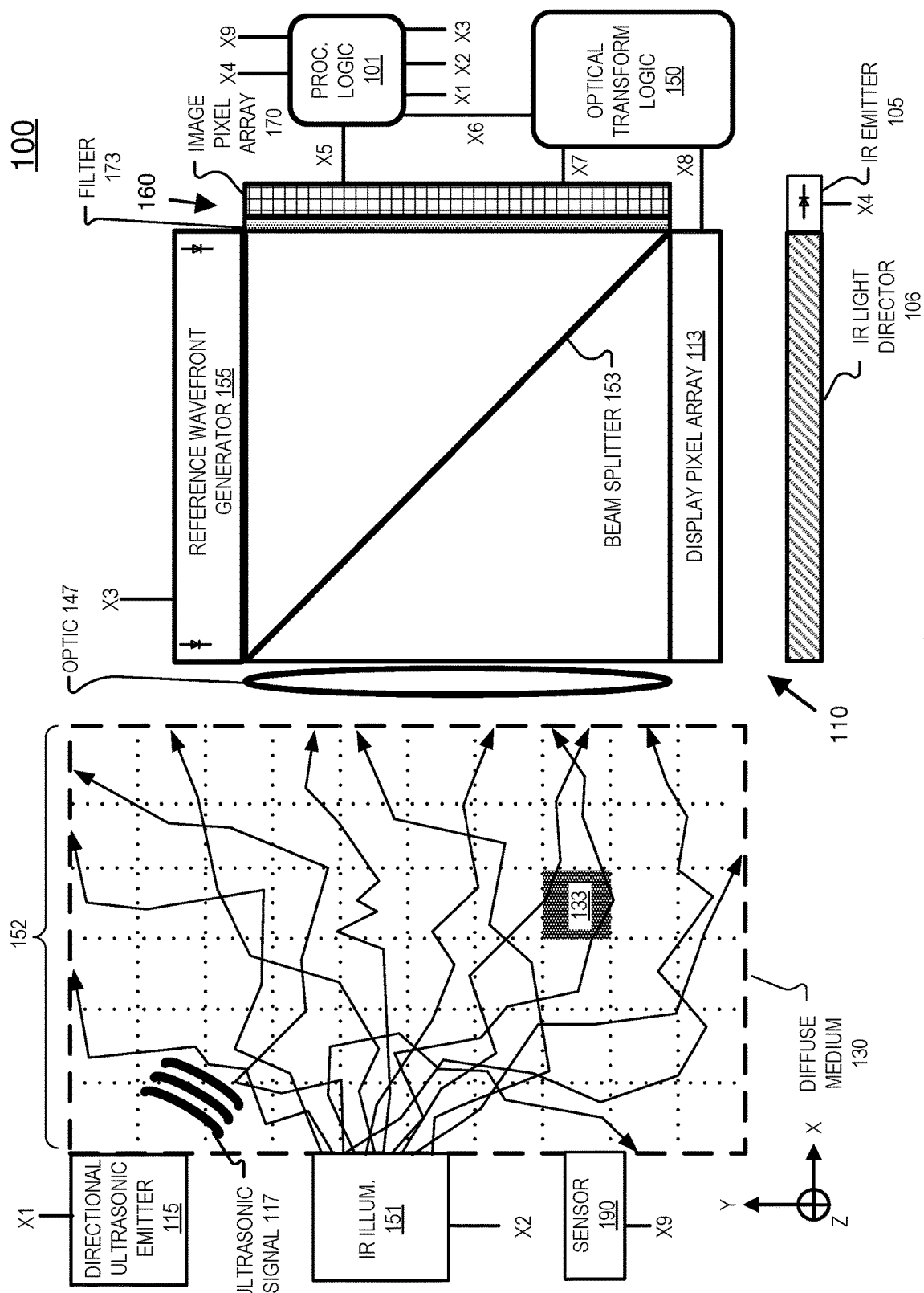
FIGS. 1A-1C illustrate an example imaging system that includes a display pixel array, an image pixel array, and a beam splitter, in accordance with an embodiment of the disclosure.

Embodiments of a system and device for optical imaging with flexible tips are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

This disclosure will generally describe imaging a diffuse medium in the context of human tissue in the medical context, however, the content of this disclosure may be applied to medical imaging, navigation, security, scientific research, or other contexts that image diffuse mediums or objects.

Human tissue is translucent to infrared light and to at least some wavelengths of visible light, although different parts of the human body (e.g. skin, blood, bone) exhibit different absorption coefficients. Researchers have attempted to use the properties of infrared light for medical imaging purposes, but size and cost constraints have been prohibitive for wide-scale adoption. Illuminating tissue and other diffuse mediums with visible light and near-infrared light for imaging purposes is sometimes referred to as Diffuse Optical Tomography. In one Diffuse Optical Tomography technique, time-of-flight (TOF) imaging can theoretically be employed by measuring the time it takes for "ballistic" photons (those photons that are not scattered) to pass through tissue. Since the ballistic photons reach the sensor the fastest, they are the least scattered (have the shortest optical path) and thus some conclusion can be drawn to create an image of the tissue that is illuminated by infrared light. However, TOF imaging generally requires specialty hardware (e.g. picosecond pulsed lasers and single photon detectors) to facilitate ultra-fast shutters on sensors that are able to image at the speed of light and the systems are overall very expensive and bulky. TOF imaging also requires an input of approximately 10-100 fold (or more) light intensity into the body than is received at the detector. Thus, efficacy and power limitations as well as safety limits on input intensity limit TOF imaging resolution, depth and utility.

In contrast to TOF imaging, some embodiments of the disclosure may illuminate a diffuse medium with an infrared light while an ultrasound emitter is focused on a particular voxel. The light used to illuminate the diffuse medium may be a light pulse generated by a pulsed light source such as a pulsed laser, for example. The infrared light propagating through the voxel may be wavelength-shifted by the ultrasonic signal and a wavelength-shifted exit signal may exit the diffuse medium. The wavelength-shifted exit signal may be interfered with a reference beam of the same wavelength and an image sensor may capture an interference pattern generated by the reference beam interfering with the wavelength-shifted exit signal. Characteristics or properties of the voxel may be determined from the captured inference pattern.

In some embodiments, a hologram is generated from the captured interference pattern and the hologram is driven onto a display pixel array illuminated with infrared light having the same wavelength as the reference beam. The illuminated hologram generates a time-reversed signal that illuminates the voxel and an exit signal of the time-reversed signal is measured to determine characteristics or properties of the voxel. Hence, optical imaging systems may include one or more of light sources, image sensors, reference beam sources, ultrasonic emitters, and other components. It may be advantageous to space out some of these components to improve imaging or to acquire multiple images. Yet, many of the components need contact access or near-contact access to the diffuse medium. For example, the one or more ultrasonic emitters and infrared sources will require contact or near-contact with the diffuse medium to emit the ultrasonic signal and illumination signals into the diffuse medium. Similarly, the image sensor will need close proximity to the diffuse medium to receive the wavelength-shifted exit signal.

In example imaging devices and systems of the disclosure, flexible members having tips at the end of them are used to position components of the imaging device or system close to the diffuse medium (e.g. tissue). The flexible members may be curved inward and the position of the tips on the ends of the flexible members may expand outward when tissue is placed between the tips as the tissue exerts outward pressure on the tips. Components of the imaging device or system that need close access to the diffuse medium are included in the tips so that the small amount of pressure on the tips (via the flexible members) presses the imaging components quite close to the diffuse medium. For imaging components that require light with precise constraints (e.g. narrowband laser pulses), optical fibers may run down the flexible members to the tips to provide the light to the components. In the medical context, the light may be generated by a laser source that is able to be placed away from the tissue so that the size or weight of the laser does not constrain the imaging component's access to the tissue. These embodiments and others will be described in more detail with references to FIGS. 1A-6.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Throughout this specification, several terms of art are used. These terms are to take on their ordinary meaning in the art from which they come, unless specifically defined herein or the context of their use would clearly suggest otherwise. For the purposes of the disclosure, visible light has a wavelength from approximately 400 nm to 780 nm and near-infrared light has a wavelength from approximately 700 nm to 3000 nm.

Figure 1B:
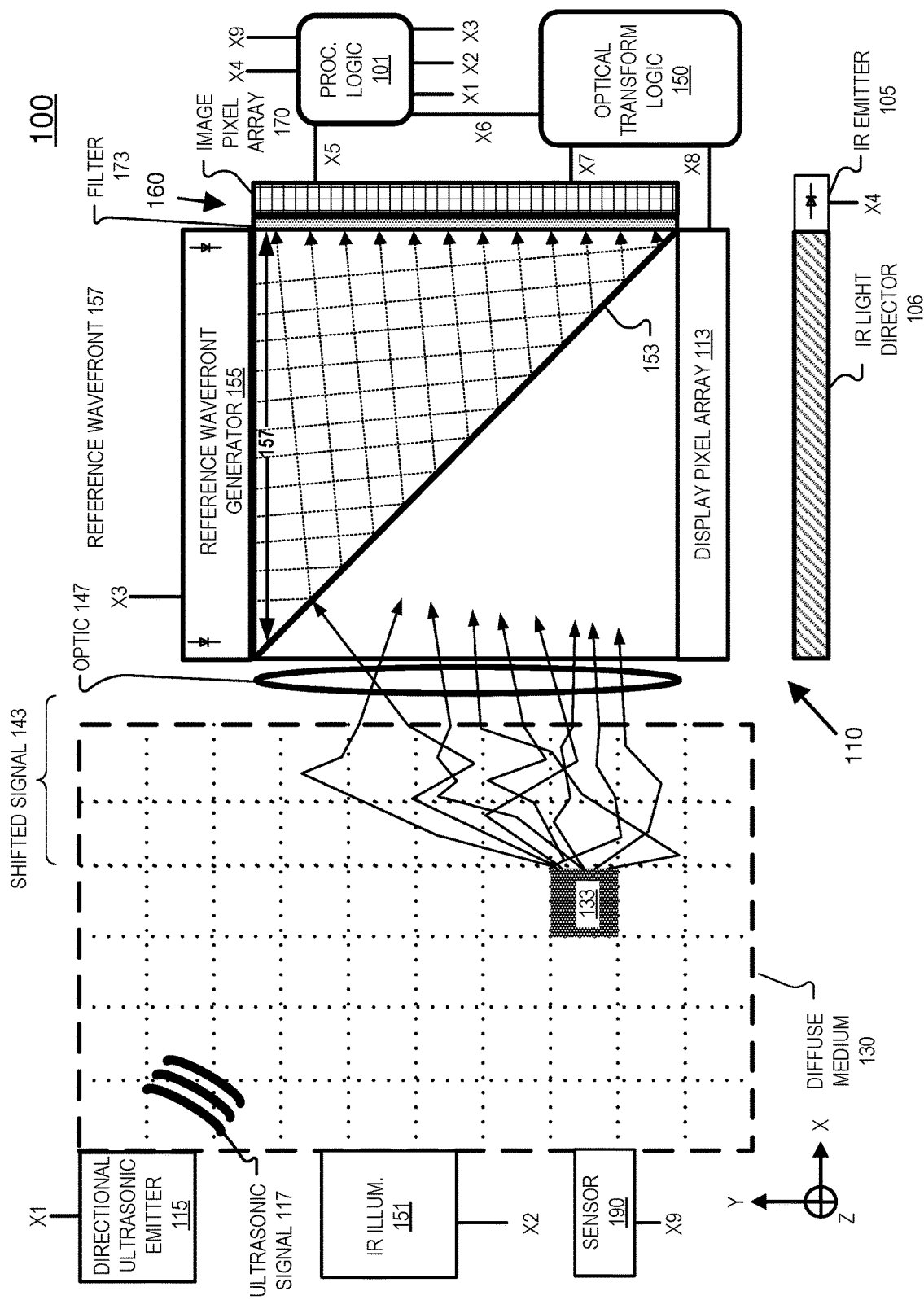
Figure 1C:
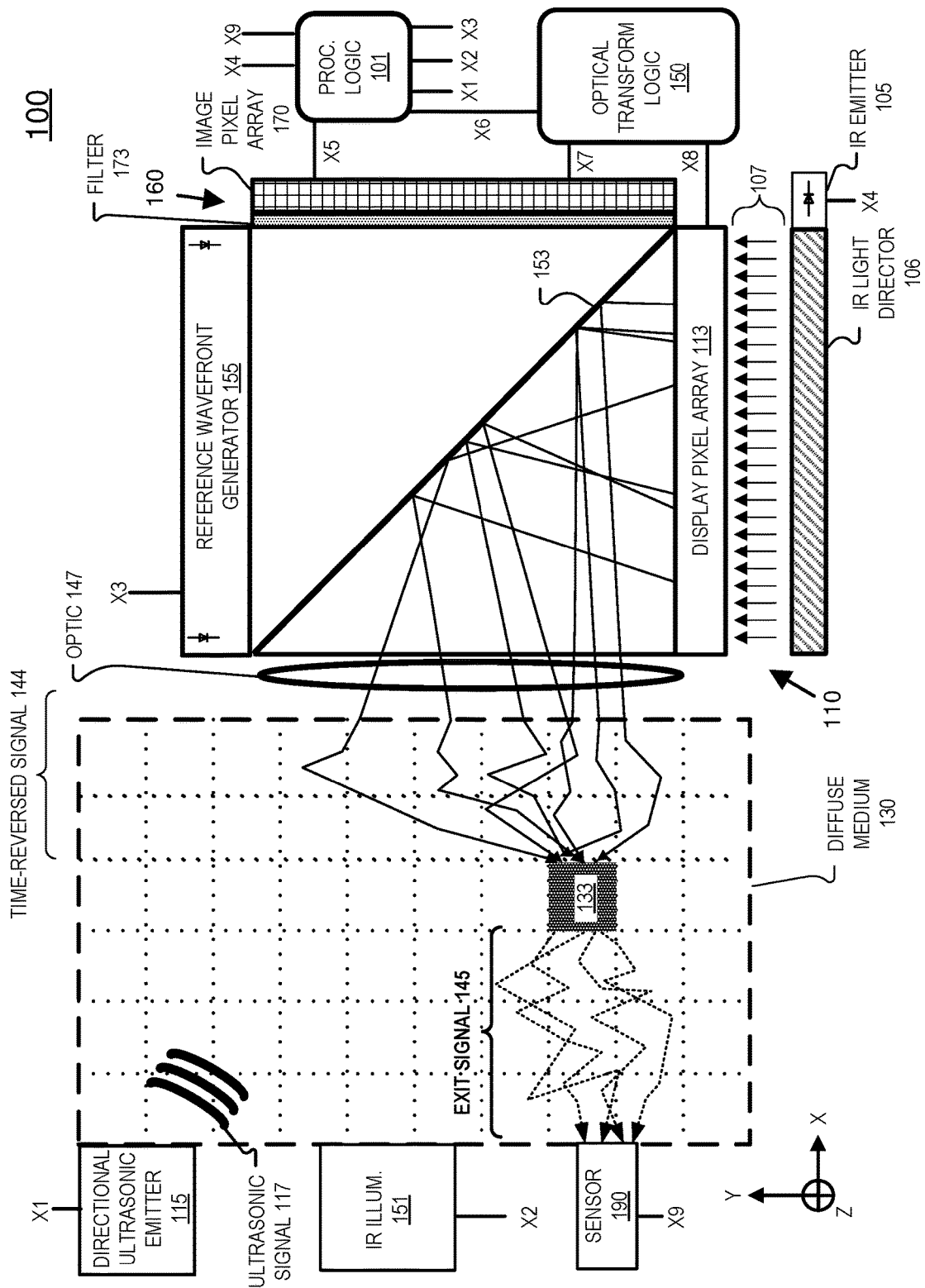

FIGS. 1A-1C illustrate an example imaging system that includes a display pixel array, an image pixel array, and a beam splitter, in accordance with an embodiment of the disclosure. In FIG. 1A, imaging system 100 includes processing logic 101, a spatial light modulator (SLM) 110, and image module 160. Imaging module 160 includes image pixel array 170 and filter(s) 173. In FIG. 1A, imaging system 100 also includes a directional ultrasonic emitter 115 coupled to be driven by processing logic 101. In FIG. 1A, SLM 110 includes an infrared emitter 105, an infrared light director 106, and a display pixel array 113. Display pixel array 113 may be an LCD (liquid crystal display), for example. The LCD display may be an active-matrix (using thin-film-transistors) or a passive matrix LCD. In one embodiment, the LCD display has pixels that are smaller than 7 microns. In other embodiments, SLM 110 may include a reflective architecture such as a liquid-crystal-on silicon (LCOS) display being illuminated by infrared light, for example. Other known transmissive and reflective display technologies may also be utilized as SLM 110. System 100 may include a plurality of discrete devices that incorporate components of system 100, in some embodiments.

Processing logic 101 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 101 to store instructions to execute operations and/or store data. A "memory" or "memories" described in this disclosure may include volatile or non-volatile memory architectures.

System 100 includes an infrared illuminator 151. Processing logic 101 is coupled to selectively activate IR illuminator 151 via output X2, in the illustrated embodiment. Infrared illuminator 151 may include an infrared laser generating a general illumination emission 152. Of course, an infrared laser may generate monochromatic coherent infrared light. Monochromatic light may be defined as light within a 4 nm frequency band, for example. The infrared light that IR illuminator 151 emits may be centered around a frequency in the 680-1000 nm range. In one embodiment, the infrared light that IR illuminator 151 emits may be centered around a frequency in the 1600-1700 nm range. In one example, IR illuminator 151 generates monochromatic light centered around 680 nm. In one example, IR illuminator 151 generates monochromatic light centered around 850 nm. The infrared illuminator 151 is disposed to direct the general illumination emission 152 into the diffuse medium 130. In the context of tissue, general illumination emission 152 will be significantly scattered within tissue within as little as 1 cm of depth into the tissue when tissue is the diffuse medium 130. At least a portion of the general illumination emission 152 will encounter voxel 133, as illustrated in FIG. 1A.

System 100 also includes an ultrasonic emitter 115. Ultrasonic emitter 115 is configured to focus an ultrasonic signal 117 to a point in three-dimensional space. In the medical context, the ultrasonic emitter 115 is configured to focus an ultrasonic signal 117 to a voxel within the human body. The voxel may be within the brain, abdomen, or uterus, for example. Processing logic 101 is coupled to drive directional ultrasonic emitter 115 to focus ultrasonic signal 117 to different locations in three-dimensional space via output X1, in the illustrated embodiment. The directional ultrasonic emitter 115 can be driven to focus an ultrasonic signal to voxel 133 in three-dimensional diffuse medium 130, for example. Focusing an ultrasonic signal 117 to a given voxel of tissue (e.g. voxel 133) influences the portion of illumination emission 152 that encounters the voxel by wavelength-shifting that portion of illumination emission 152 that propagates through that voxel.

In FIG. 1B, the wavelength-shifted portion of the general illumination emission 152 is illustrated as shifted infrared imaging signal 143. Being influenced by ultrasonic signal 117, shifted signal 143 has a different wavelength (hereinafter referred to as lambda-two) than general illumination emission 152 (referred to as lambda-one). In some embodiments, the delta between lambda-one and lambda-two may be less than 1 nanometer. In an embodiment, the delta between lambda-one and lambda-two may be less than 20 femtometer.

System 100 receives (at least a portion of) shifted infrared imaging signal 143. An input optic 147 may optionally be included in system 100. Input optic 147 may receive shifted signal 143 and direct the shifted signal 143 to be incident on image pixel array 170. In one embodiment, input optic 147 is configured to filter out an angled portion of the shifted signal 143. In one embodiment, the angled portion of the shifted signal 143 has a plus-or-minus angle of incidence upon the input optic 147 that is higher than an angle threshold. In one embodiment, the sine of twice the angle threshold is approximately equivalent to a wavelength of the shifted signal 143 (lambda-two) divided by twice a distance between two pixels of the image pixel array 170. In one embodiment, the angle threshold is between five and seven degrees.

Still referring to FIG. 1B, reference wavefront generator 155 generates an infrared reference wavefront 157 having the lambda-two wavelength so that infrared reference wavefront 157 interferes with the incoming shifted signal 143. Reference wavefront generator 155 may include one or more laser diodes and corresponding optics to generate a substantially uniform wavefront. Processing logic 101 is coupled to selectively activate reference wavefront generator 155 via output X3, in the illustrated embodiment.

A first portion of the infrared reference wavefront 157 is redirected to the image pixel array 170 by beam splitter 153 while a second remaining portion of wavefront 157 passes through beam splitter 153. Shifted signal 143 encounters beam splitter 153 and a first portion of the shifted signal 143 passes through beam splitter 153 while the remaining second portion of the shifted signal 143 is reflected by beam splitter 153. The first portion of the shifted signal 143 that passes through beam splitter 153 interferes with the first portion of wavefront 157 that is redirected to image pixel array 170 and image pixel array 170 captures an infrared image of the interference between shifted signal 143 and infrared reference wavefront 157.

In one embodiment, reference wavefront generator 155 is disposed to deliver the infrared reference wavefront 157 to the image pixel array 170 at an angle to a pixel plane of the image pixel array 170. Image array 170 may include image pixels disposed in a two-dimensional rows and columns that define the pixel plane of the image pixel array 170. In one embodiment, the angle is between five and seven degrees so that the infrared reference wavefront 157 encounters the image pixels of image pixel array 170 at a non-orthogonal angle. Angling the infrared reference wavefront 157 may change the interference orientation and size between shifted signal 143 and wavefront 157, which may enable better signal isolation at the image pixel array 170. Processing logic 101 is coupled to initiate the image capture by image pixel array 170 via output X5, in the illustrated embodiment.

A linear polarizer may be included in system 100 to polarize shifted signal 143 to have the same polarization orientation as infrared reference wavefront 157. The light source of reference wavefront generator 155 may generate linear polarized light which imparts a polarization orientation to infrared reference wavefront 157. The linear polarizer may be included in optic 147, filter 173, or in a linear polarizer disposed between optic 147 and filter 173.

In the illustrated embodiment, an infrared filter 173 is disposed between beam splitter 153 and image pixel array 170. Infrared filter 173 may pass the wavelength of infrared light emitted by reference wavefront generator 155 (lamda-two) and reject ambient light in a bandpass that is 10 nm or greater.

Image pixel array 170 may be implemented with an a-Si (amorphous Silicon) thin film transistors, in some embodiments or a CMOS (Complimentary Metal-Oxide-Semiconductor) image sensor, in some embodiments. Image pixel array 170 can be a commercially available image sensor. In one embodiment, image pixel array 170 has image pixels having a pixel pitch of 3.45 microns. In one embodiment, image pixel array 170 has image pixels having a pixel pitch of 1.67 microns. The pixel resolution of image pixel array 170 may vary depending on the application. In one embodiment, the image pixel array 170 is 1920 pixels by 1080 pixels. In one embodiment, the image pixel array is 40 Megapixels or more. Image pixel array 170 can capture an infrared image of an interference between shifted signal 143 and IR reference wavefront 157 by measuring the image charge generated in each pixel during a given integration period that is determined by an electronic shutter. The electronic shutter may be a global shutter (where each pixel measures the incident light during a same time period) or a rolling shutter. The electronic shutter can be actuated by processing logic 101 via input/output X5. Input/output X5 may include digital input/output lines as well as a data bus. Image pixel array 170 is communicatively coupled to optical transform logic 150 to send the captured infrared image(s) to optical transform logic 150 for further processing. In some embodiments, the integration period of the pixels of the image pixel array 170 is determined by the length of a laser pulse. Image pixel array 170 may include a local (on-board) digital signal processor (DSP), in some embodiments, and optical transform logic 150 may receive the captured infrared images from the DSP.

Optical transform logic 150 is coupled to image pixel array 170 via communication channel X7, in the illustrated embodiment. Optical transform logic is also communicatively coupled to processing logic 101 via communication channel X6. Optical transform logic 150 is coupled to receive the captured infrared image from the image pixel array and provide a holographic pattern to be driven onto the display pixel array 113. The optical transform logic 150 is configured to extract phase data of the interference captured by the infrared image and the holographic pattern is generated from the phase data. A more detailed description of example optical transform logic is described in U.S. patent application Ser. No. 15/942,480, which is hereby incorporated by reference.

Referring now to FIG. 1C, display pixel array 113 is configured to generate an infrared holographic imaging signal 144 (reconstruction of signal 143) according to a holographic pattern driven onto the array 113. Optical transform logic 150 is coupled to provide the array 113 the holographic pattern via communication channel X8.

In FIG. 1C, display pixel array 113 is illustrated as a transmissive LCD that is illuminated by infrared wavefront 107. In the illustrated embodiment, infrared (IR) emitter 105 is coupled to be driven by output X4 of processing logic 101. When processing logic 101 turns on (activates) IR emitter 105, infrared light propagates into IR light director 106. IR light director 106 may be a light guide plate similar to those found in conventional edge lit LCDs. IR light director 106 may be a slim prism utilizing TIR (total internal reflection). IR light director 106 redirects the infrared light toward display pixel array 113. IR light director 106 may include a sawtooth grating to redirect the infrared light toward array 113. IR emitter 105 is an infrared laser diode that emits monochromatic infrared light, in one embodiment.

Steerable infrared beams can be generated by SLM 110 by driving different holographic patterns onto display pixel array 113. Each different holographic pattern can steer (focus) the infrared light in a different direction. The directional nature of the infrared beam is influenced by the constructive and destructive interference of the infrared light emitted from the pixels of SLM 110. As an example, a holographic pattern that includes different "slits" at different locations can generate different infrared beams. The "slits" can be generated by driving all the pixels in the display pixel array 113 to "black" (not transmissive) except for the pixels where the "slits" are located are driven to be "white" (transmissive) to let the infrared light propagate through. The pixel size of display pixel array 113 may be 1 micron, although in some embodiments pixels sized up to 10 times the wavelength of the infrared light can be used. In one example, if IR emitter 105 is an 850 nm laser diode, the pixel size of SLM 110 may be 850 nm. The pixel size influences the angular spread of a hologram since the angular spread is given by the Grating Equation:

$$\sin(\theta) = m\lambda/d \quad \text{(Equation 1)}$$

where θ is the angular spread of light, m is an integer number and the order of diffraction, and d is the distance of two pixels (a period). Hence, smaller pixel size generally yields more design freedom for generating holographic beams, although pixels sizes that are greater than the wavelength of light can also be used to generate holographic imaging signals. Display pixel array 113 may include square pixels (rather than the rectangular pixels in conventional RGB LCDs) so that the Grating Equation is applicable in both the row dimension and column dimension of the display pixel array 113.

In the illustrated embodiment, processing logic 101 selectively activates infrared emitter 105 and infrared light director 106 directs the infrared light to illuminate display pixel array 113 as infrared wavefront 107 while the holographic pattern is driven onto array 113. Infrared wavefront 107 is the same wavelength as infrared reference wavefront 157. Processing logic 101 may deactivate reference wavefront generator 155 while display pixel array 113 is being illuminated by infrared wavefront 107. Processing logic 101 may be configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Display pixel array 113 generates an infrared holographic imaging signal when the holographic pattern is illuminated by infrared wavefront 107 and the infrared holographic imaging signal is redirected by beam splitter 153 to exit system 100 as a reconstruction 144 (in reverse) of the shifted signal 143 that entered system 100. Reconstructed signal 144 follows (in reverse) whatever scattered path that shifted signal 143 took from voxel 133 to beam splitter 153 so reconstructed signal 144 is essentially "focused" back onto voxel 133.

Voxel 133 may absorb or scatter reconstructed signal 144 according to biological and/or optical characteristics of voxel 133 and sensors may measure an exit signal 145 of the reconstructed signal 144 that encounters voxel 133. System 100 may optionally include a sensor 190 coupled to processing logic 101 via an input/output X9 to initiate light measurement of exit signal 145 and pass the light measurement to processing logic 101. Although exit signal 145 is illustrated as being directed to sensor 190, the illustrated exit signal 145 is only a portion of the exit signal 145 that will be generated from signal 144 encountering voxel 133 and exit signal 145 will have many exit points from diffuse medium in addition to the illustrated portion of exit signal 145. The sensors that measure this exit signal may simply measure the amplitude of the exit signal. Sensor 190 may be a photodiode or a CMOS image sensor, for example. In one embodiment, the image pixel array 170 is used to measure the amplitude and/or phase of exit signal 145. The amplitude and/or phase of the exit signal 145 may be used to generate an image of diffuse medium 130. A reconstructed signal 144 may be directed to voxel 133 multiple times (with multiple corresponding measurements of exit signal 145) so that biological changes in voxel 133 may be recorded over a time range.

System 100 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array gives display pixel array 113 the ability to generate steerable holographic infrared beams that can focus an infrared signal (e.g. 144) to different voxels in three-dimensional space to facilitate the raster scanning of diffuse medium 130.

In one embodiment, processing logic 101 is configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Figure 2A:
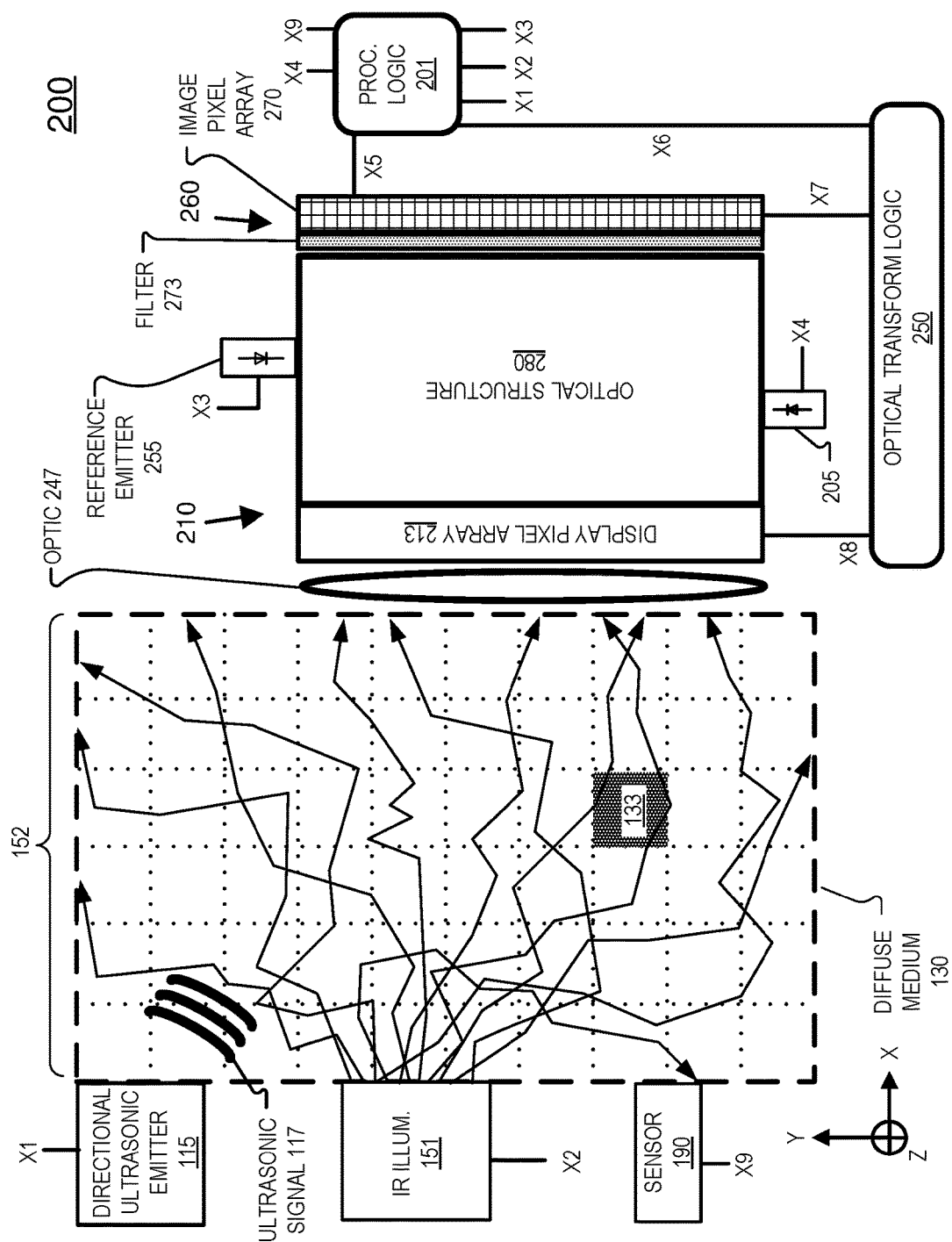
FIGS. 2A-2C illustrate an example imaging system that includes an image pixel array receiving an exit signal through a display pixel array, in accordance with an embodiment of the disclosure.
Figure 2B:
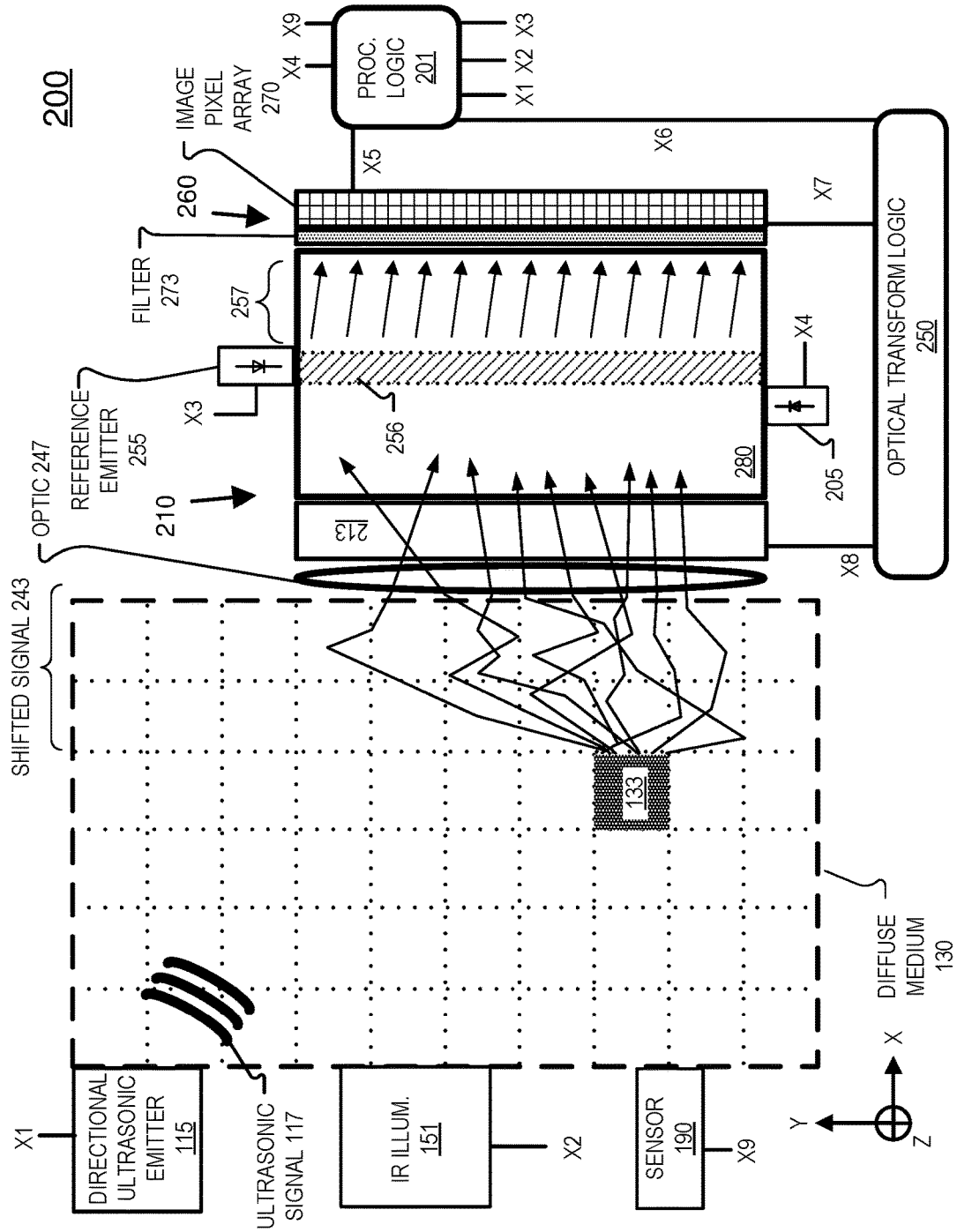
Figure 2C:
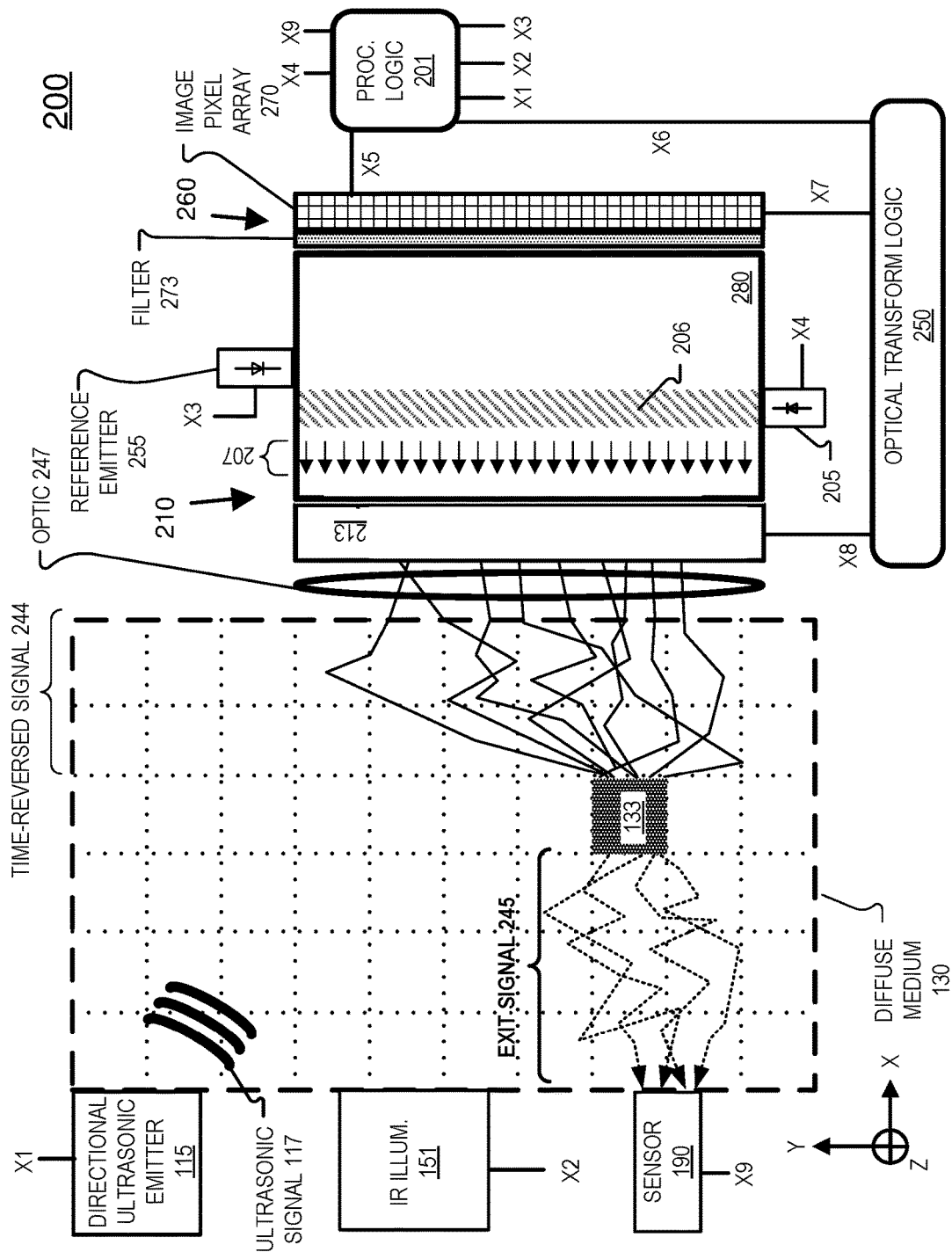

FIGS. 2A-2C illustrate an example imaging system 200 that includes an optical structure disposed between a display pixel array and an image pixel array, in accordance with an embodiment of the disclosure. System 200 illustrated in FIGS. 2A-2C functions similarly to system 100 of FIGS. 1A-1C although there are differences associated with the different positioning of the SLM 210, the imaging module 260, and the addition of optical structure 280.

Similarly to FIG. 1A, in FIG. 2A, processing logic 201 is coupled to drive directional ultrasonic emitter 115 to focus ultrasonic signal 117 to different locations in three-dimensional space, via output X1. Processing logic 201 is also coupled to selectively activate IR illuminator 151 via output X2, in the illustrated embodiment. System 200 may include a plurality of discrete devices that incorporate components of system 200, in some embodiments.

Imaging module 260 includes image pixel array 270 and filter(s) 273. In FIG. 2A, imaging system 200 also includes a directional ultrasonic emitter 115 coupled to be driven by processing logic 201. SLM 210 includes an infrared emitter 205, an infrared light director 206 (illustrated in FIG. 2C), and a display pixel array 213. Display pixel array 213 is a transmissive pixel array, in FIG. 2A.

Processing logic 201 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 201 to store instructions to execute operations and/or store data. A "memory" or "memories" described in this disclosure may include volatile or non-volatile memory architectures.

With ultrasonic signal 117 focused on voxel 133 in diffuse medium 130, IR illuminator 151 is selectively activated to emit general illumination emission 152 and a portion of emission 152 encounters voxel 133.

In FIG. 2B, the wavelength-shifted portion of the general illumination emission 152 is illustrated as shifted infrared imaging signal 243. Being influenced by ultrasonic signal 117, shifted infrared imaging signal 243 has a different wavelength (lambda-two) than general illumination emission 152 (lambda-one).

System 200 receives (at least a portion of) shifted signal 243. An input optic 247 may optionally be included in system 200. Input optic 247 may receive shifted signal 243 and focus the shifted signal 243 to be incident on image pixel array 270. In one embodiment, input optic 247 is configured to filter out an angled portion of the shifted signal 243, as described with regard to an embodiment of input optic 147.

Still referring to FIG. 2B, reference emitter 255 is configured to selectively emit an infrared reference light having the lambda-two wavelength so that infrared reference wavefront 257 interferes with the incoming shifted signal 243. Reference emitter 255 may include one or more laser diodes and reference director optic 256 in optical structure 280 may direct the lambda-two infrared reference light to image pixel array 270 as a substantially uniform infrared reference wavefront 257. Processing logic 201 is coupled to selectively activate reference emitter 255 via output X3, in the illustrated embodiment.

A linear polarizer may be included in system 200 to polarize shifted signal 243 to have the same polarization orientation as infrared reference wavefront 257. Reference emitter 255 may generate linear polarized light which imparts a polarization orientation to infrared reference wavefront 257. The linear polarizer may be included in optic 247, filter 273, or optical structure 280.

Shifted signal 243 may encounter input optic 247, display pixel array 213, and optical structure 280 prior to becoming incident upon image pixel array 270. The shifted signal 243 interferes with infrared reference wavefront 257 and image pixel array 270 captures an infrared image of the interference between shifted signal 243 and infrared reference wavefront 257. To allow shifted signal 243 to pass through display pixel array 213, each of the display pixels of the display pixel array 213 may be driven to a transmissive state while IR illuminator 151 and reference emitter 255 are activated.

In one embodiment, reference director optic 256 is configured to deliver the infrared reference wavefront 257 to the image pixel array 270 at an angle to a pixel plane of the image pixel array 270. Processing logic 201 is coupled to initiate the image capture by image pixel array 270 via output X5, in the illustrated embodiment.

In the illustrated embodiment, an infrared filter 273 is disposed between optical structure 280 and image pixel array 270. Infrared filter 273 may include the same configuration as infrared filter 173. Image pixel array 270 may include the same configuration as image pixel array 170. Image pixel array 270 is communicatively coupled to optical transform logic 250 to send the captured infrared image(s) to optical transform logic 250 for further processing. Optical transform logic 250 is coupled to image pixel array 270 via communication channel X7, in the illustrated embodiment. Optical transform logic 250 is coupled to receive the captured infrared image from the image pixel array 270 and provide a holographic pattern to be driven onto the display pixel array 213. The optical transform logic 250 is configured to extract phase data of the interference captured by the infrared image and the holographic pattern is generated from the phase data.

Referring now to FIG. 2C, display pixel array 213 is configured to generate an infrared holographic imaging signal 244 according to a holographic pattern driven onto the array 213. Optical transform logic 250 is coupled to provide the array 213 the holographic pattern to array 213 via communication channel X8.

In FIG. 2C, display pixel array 213 is illustrated as a transmissive LCD that is illuminated by infrared wavefront 207. In the illustrated embodiment, infrared emitter 205 is coupled to be driven by output X4 of processing logic 201. When processing logic 201 turns on (activates) IR emitter 205, infrared light propagates into IR light director 206. IR light director 206 redirects the infrared light toward display pixel array 213. IR emitter 205 is an infrared laser diode that emits monochromatic infrared light, in one embodiment.

In the illustrated embodiment, processing logic 201 selectively activates infrared emitter 205 and infrared light director 206 directs the infrared light to illuminate display pixel array 213 as infrared wavefront 207 while the holographic pattern is driven onto array 213. Infrared wavefront 207 is the same wavelength as infrared reference wavefront 257. Processing logic 201 may deactivate reference emitter 255 while display pixel array 213 is being illuminated by infrared wavefront 207. Processing logic 201 may be configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

Display pixel array 213 generates an infrared holographic imaging signal 244 when the holographic pattern is illuminated by infrared wavefront 207 and the infrared holographic imaging signal 244 exits system 200 as a reconstruction (in reverse) of the shifted signal 243 that entered system 200. Reconstructed signal 244 follows (in reverse) whatever scattered path that shifted signal 243 took from voxel 133 to the display pixel array 213 so reconstructed signal 244 is essentially "focused" back onto voxel 133.

Voxel 133 may absorb or scatter reconstructed signal 244 according to biological characteristics of voxel 133 and sensors may measure an exit signal 245 of the reconstructed signal 244 that encounters voxel 133. System 200 may optionally include a sensor 190 coupled to processing logic 201 via an input/output X9 to initiate light measurement of exit signal 245 and pass the light measurement to processing logic 201. Although exit signal 245 is illustrated as being directed to sensor 190, the illustrated exit signal 245 is only a portion of the exit signal 245 that will be generated from signal 244 encountering voxel 133 and exit signal 245 will have many exit points from diffuse medium in addition to the illustrated portion of exit signal 245. The sensors that measure this exit signal may simply measure the amplitude of the exit signal. In one embodiment, the image pixel array 270 is used to measure the amplitude and/or phase of exit signal 245. The amplitude and/or phase of the exit signal 245 may be used to generate an image of diffuse medium 130. A reconstructed signal 244 may be directed to voxel 133 multiple times (with multiple corresponding measurements of exit signal 245) so that biological changes in voxel 133 may be recorded over a time range.

System 200 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array 213 gives display pixel array 213 the ability to generate steerable holographic infrared beams that can focus the reconstructed signal (e.g. 244) to different voxels in three-dimensional space to facilitate the raster scanning of diffuse medium 130.

In one embodiment, processing logic 201 is configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

In system 200, image pixel array 270 is disposed in a parallel plane to display pixel array 213. However, in some embodiments, image pixel array 270 may be angled to increase the signal of interference between the infrared reference wavefront 257 and shifted signal 243. In system 100, image pixel array 170 is illustrated as being in a plane that is orthogonal to display pixel array 113. However, in some embodiment, image pixel array 170 may be angled to increase the signal of interference between the infrared reference wavefront 157 and shifted signal 143.

Although not specifically illustrated in FIGS. 1A-2C, infrared illuminator 151, reference wavefront generator 155 and infrared emitter 105 may be fiber optic outputs that are provided light via fiber optic from a single laser source. Similarly, infrared illuminator 151, reference emitter 255, and infrared emitter 205 may be provided light via fiber optic from a single laser source. The light from the single laser source may be modulated (e.g. by an acoustic optical modulator) to direct the laser light to the proper fiber optic for illumination. A micro-electro-mechanical system (MEMS) mirror, a digital micromirror device (DMD), or a mirror galvanometer may be used to selectively couple light from a single source into different fiber optic paths, in different embodiments. The light from the single laser source may also be selectively wavelength-shifted (e.g. by an acoustic optical modulator) to provide IR illuminator 151 with lambda-one wavelength light and to provide reference elements 105, 205, 155, and 255 with lambda-two wavelength light.

Figure 3:
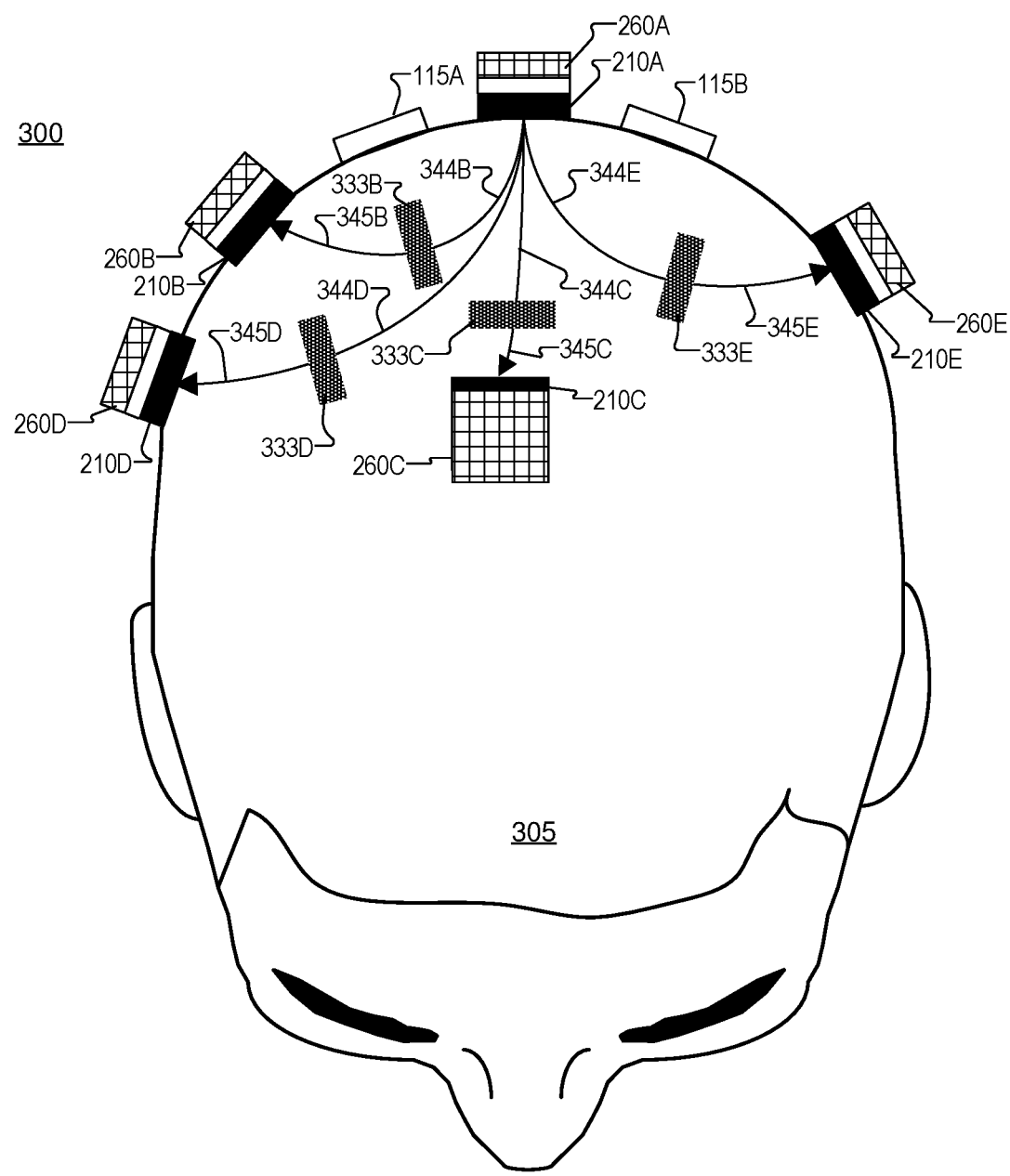
FIG. 3 illustrates an example placement of components of an imaging system in relationship to a human head, in accordance with an embodiment of the disclosure.

FIG. 3 illustrates an example placement of components of an imaging system 300 in relationship to a human head, in accordance with an embodiment of the disclosure. FIG. 3 is a top-down view of a human head 305. Imaging system 300 includes SLMs 210A-210E and imaging modules 260A-260E arranged as in system 200, and directional ultrasonic emitters 115A and 115B. Of course, SLMs 110 and imaging modules 160 may also be used instead of SLMs 210 and imaging modules 260 in imaging system 300. FIG. 3 shows that SLM 210A may generate multiple reconstructed infrared signals 344 that are directed to image different voxels 333 of the brain while the exit signals 345 are imaged by different imaging modules 260. The other SLMs 210B-210E may also generate reconstructed infrared signals 344 (not illustrated) directed to voxels where the exit signals are imaged by each of imaging modules 260A-E. Scientific literature suggests that the penetration depth of infrared light into tissue is around 10 cm so multiple SLMs 210 and imaging modules 160 may be needed to image the entire brain or other tissue. Although not illustrated, sensors 190 may also be placed around a diffuse medium such as human head 305 to measure the exit signals 345. A wearable hat may include system 300 so that system 300 can be worn as a wearable, in some embodiments. Other wearables may also include all or part of system 300.

Figure 4:
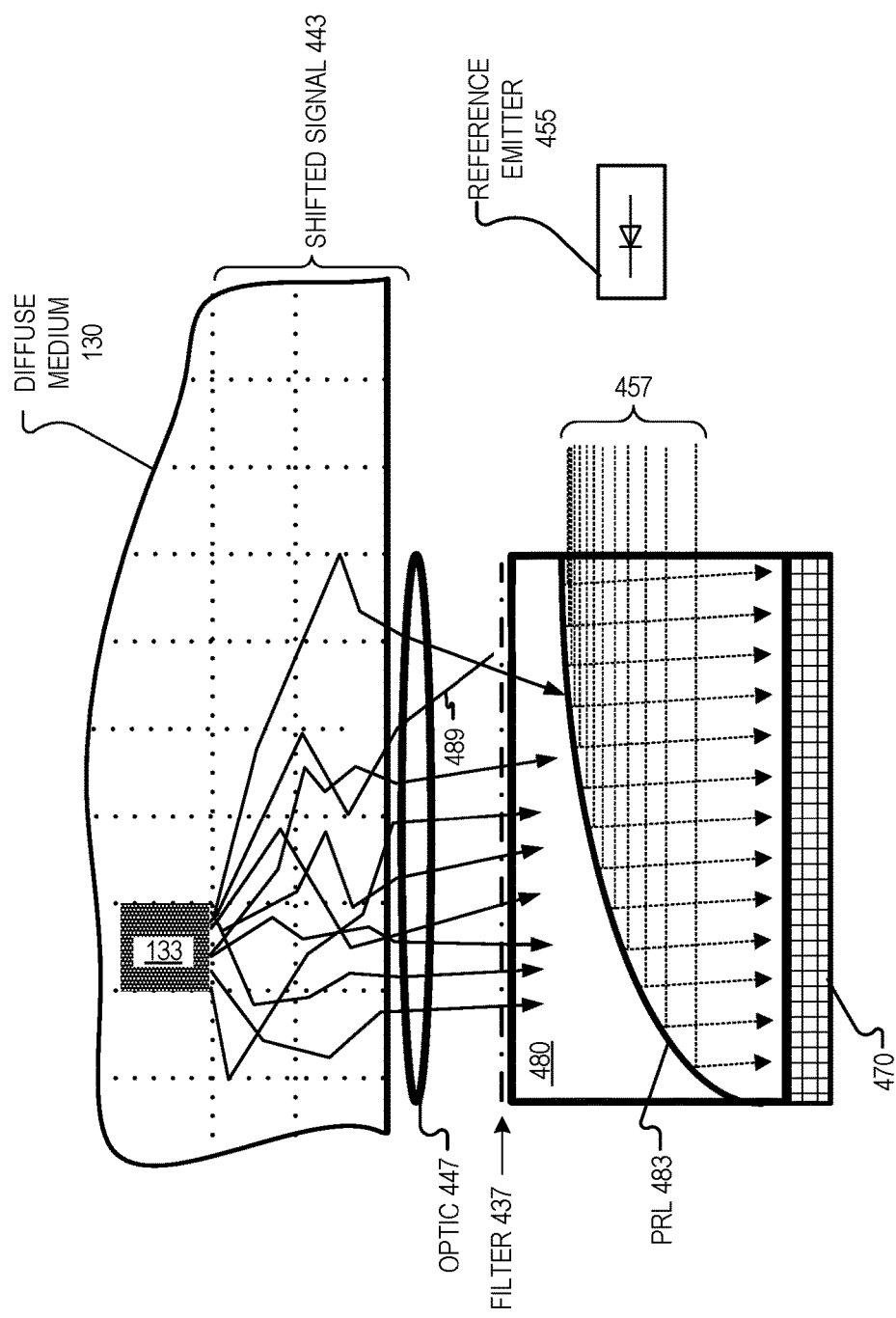
FIG. 4 illustrates an example imaging device having a partially reflective layer for directing an infrared reference beam, in accordance with an embodiment of the disclosure.

FIG. 4 illustrates an example imaging device 400 that includes example interference optics for interfering a reference beam with a wavelength-shifted exit signal, in accordance with an embodiment of the disclosure. Device 400 includes a sensor 470, optical structure 480, and infrared reference emitter 455. Sensor 470 may include a two-dimensional image pixel array arranged in rows and columns that define a pixel plane of the sensor 470. Sensor 470 may be a CMOS image sensor in some embodiments. Optical structure 480 includes a partially reflective layer 483 disposed on a two-dimensional curvature. The curvature may be parabolic. In one embodiment, the curvature is an offset parabola configured to collimate a received infrared reference beam 457 and direct rays from infrared reference beam 457 to sensor 470 at an angle relative to a vector that is normal to a pixel plane of the sensor 470.

In FIG. 4, device 400 includes an infrared filtering layer 437. Infrared filtering layer 437 may be a bandpass filter that is configured to pass an infrared wavelength band of the wavelength-shifted exit signal 443 and reject ambient light. In an embodiment, the wavelength band (the passband) is less than 2 nm. In an embodiment, the wavelength band (the passband) is less than 1 nm. The bandpass filter may have a 1 nm bandpass centered around a wavelength of wavelength-shifted exit signal 443 and be approximately 1 mm thick. By using infrared filtering layer 437 to block out light besides the wavelength of wavelength-shifted exit signal 443, an interference image captured by sensor 470 may be limited to the interference between the wavelength-shifted exit signal 443 and the infrared reference beam 457.

Infrared filtering layer 437 may be disposed on a filtering plane that is parallel to the pixel plane of sensor 470. Partially reflective layer 483 is disposed between infrared filtering layer 437 and sensor 470. In the illustrated embodiment, infrared filtering layer 437 is illustrated as outside of optical structure 480. In some embodiments, infrared filtering layer 437 may be included in optical structure 480. In one embodiment, optical structure 480 includes an optically transparent material to support partially reflective layer 483 and the curvature that partially reflective layer is disposed on and the infrared filtering layer 437 may be immersed in that same refractive material. Infrared filtering layer 437 may be configured as an angle-selective infrared filtering layer that is configured to transmit rays of the wavelength-shifted exit signal 443 within an angle of incidence range and reject the rays of the wavelength-shifted exit signal that are outside of the angle of incidence range. Infrared filtering layer 437 may be disposed on a filtering plane that is parallel to a pixel plan of the sensor.

In operation, reference emitter 455 emits an infrared reference beam 457 that is the same wavelength as wavelength-shifted exit signal 443. Reference emitter 455 may be a coherent infrared illumination source (e.g. a laser) that provides the infrared reference beam to optical structure 480 by way of a fiber optic. Infrared reference beam 457 encounters partially reflective layer (PRL) 483. Shifted signal 443 also encounters PRL 483 and a portion of signal 443 passes through PRL 483 toward image pixel array 470. The portion of signal 443 that passes through PRL 483 interferes with beam 457 and image pixel array 470 captures an interference image of an interference between signal 443 and 457. Additional optics (not illustrated) may be disposed between optical structure 480 and infrared reference emitter 455 to spread infrared reference beam 457 to properly encounter partially reflective layer 483.

Device 400 may include the ultrasonic emitter 115 and infrared illuminator 151 from FIGS. 1A-2C. Device 400 may also include processing logic to synchronize the ultrasonic signal 117 and infrared illumination signal 152. A display pixel array (e.g. display pixel array 113) is not illustrated in FIG. 4 and in some embodiments of the disclosure, device 400 may be configured as a "read-only" device that does not generate a time-reversed signal such as signal 144/244. Rather, the captured interference patters are used to generate an image of the voxels 133 of the diffuse medium.

Figure 5A:
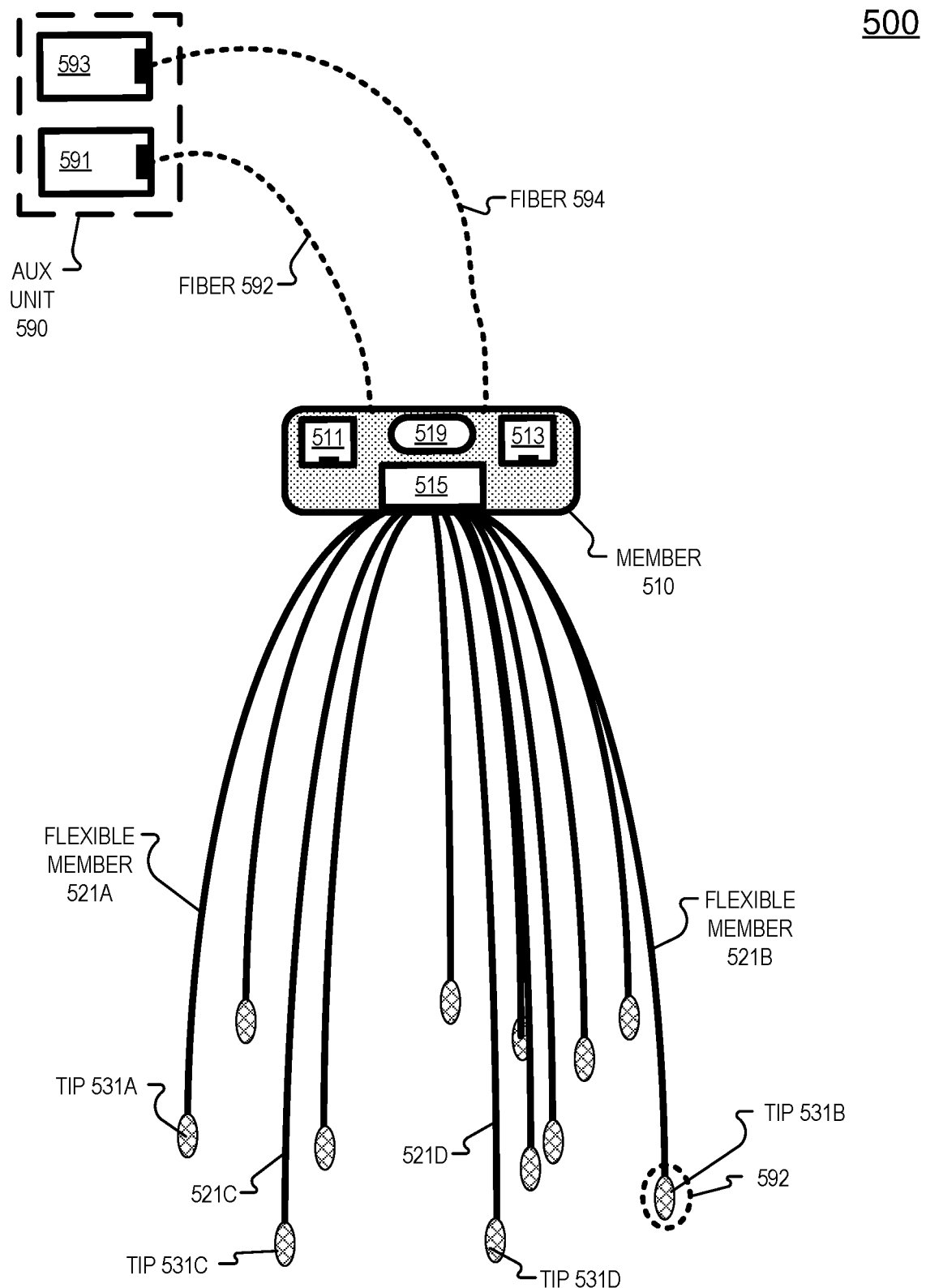
FIGS. 5A-5D illustrate an example imaging system with imaging components included in flexible tips, in accordance with an embodiment of the disclosure.

FIG. 5A illustrates an example imaging system 500 that includes imaging components in tips 531 disposed at the ends of flexible members 521, in accordance with an embodiment of the disclosure. Example system 500 includes a member structure 510 including an ultrasonic emitter 515 and light sources 511 and 513. Ultrasonic emitter 515 may be configured as a directional ultrasonic emitter similarly to ultrasonic emitter 115. Light source 511 and 513 may be infrared light sources. Optionally, system 500 also includes an auxiliary unit 590 that includes light sources 591 and 593. Light sources 591 and/or 593 may be infrared laser light sources. Light from light sources 591 and 593 is provided to member structure 510 via optical fibers 592 and 594, respectively. Auxiliary unit 590 may also include communication interfaces (either wired or wireless) and/or a power supply, in some embodiments.

Processing logic 519 is illustrated as included in member structure 510, in FIG. 5A. Processing logic 519 may be included in auxiliary unit 590, in some embodiments. Processing logic 519 may be coupled to light sources 511, 513, 591, and 593 to control/synchronize the emission of light from the light sources. Processing logic 519 is coupled to ultrasonic emitter 515 to control the timing and/or direction of the emission of ultrasonic imaging signal 517. Processing logic 519 may also be configured to control imaging components that are included in tips 531 of system 500. Processing logic 519 may send and receive data (e.g. images) from imaging components included in tips 531.

Processing logic 519 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 519 to store instructions to execute operations and/or store data. A "memory" or "memories" described in this disclosure may include volatile or non-volatile memory architectures.

A plurality of flexible members 521 are coupled to member structure 510. The flexible members 521 may be made from plastic or metal. The flexible members 521 in FIG. 5A are illustrated as having some curvature to them. The flexible members 521 may be curved inward so that the position of the tips 531 expands outward when tissue is placed between the tips 531 such that that the tissue exerts outward pressure on the tips 531. In other words, the flexible members 521 may provide spring-action that lightly presses tips 531 against a diffuse medium or tissue for imaging. Since the tips 531 are pressed against the medium for imaging, the components within the tips 531 are provided with close access to send signals into the medium and receive signals from the medium. The length of the flexible members 521 may vary so that various components of the imaging system included in tips 531 are spaced apart from each other to provide different imaging coverage for the diffuse medium. In one example, the plurality of flexible member 521 and the imaging components included in tips 531 are arranged so that when tissue is positioned in the middle of the flexible members, the imaging components in tips 531 are arranged similarly to imaging system 300. Tips 531 may include an encapsulating material to encapsulate electronics and optical structures of tips 531. The encapsulating material may be a high optical quality refractive material.

In some embodiments, a deflection of one or more of the flexible members 521 is measured for angle or distance to ascertain a position of the corresponding tip 531. In one embodiment, a spring tension sensor located in member 510 measures the tension on a particular flexible member 521 and the position of the corresponding tip 531 can be calculated from a tension value generated by the spring tension sensor. Processing logic 519 may receive the tension value from the spring tension sensor, for example. The greater the tension value, the farther the tip 531 may be from the center of an imaginary vector that is orthogonal to a first side 565 of ultrasonic emitter 515. In one embodiment, a force sensor is disposed with tip 531 and the force sensor generates a force value according to the force exerted on tip 531 by tissue exerting that force. A position of the tip 531 may be calculated from a force value generated by the force sensor. The greater the force value, the farther the tip 531 may be from the center of an imaginary vector that is orthogonal to a first side 565 of ultrasonic emitter 515.

Figure 5B:
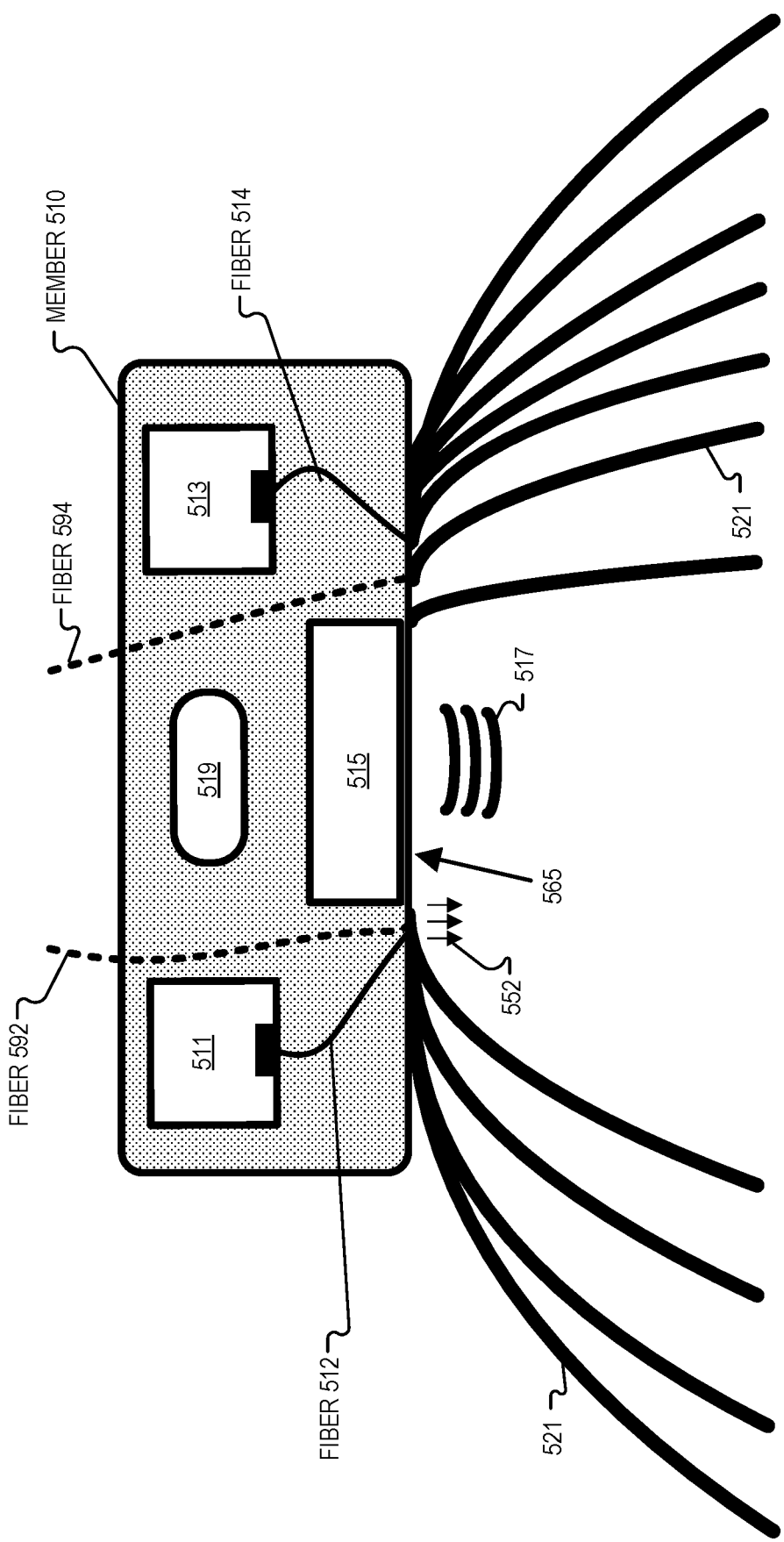

FIG. 5B illustrates a zoomed-in view of an example configuration of member structure 510, in accordance with an embodiment of the disclosure. In FIG. 5B, ultrasonic emitter 515 is configured to emit ultrasonic imaging signal 517 into tissue that is pressed against member 510. Ultrasonic emitter 515 is configured to emit the ultrasonic imaging signal 517 on a first side 565 of the member structure 510 and the flexible members are coupled to the first side of the member structure 510. Light source 511 is configured to provide infrared light to at least a portion of the flexible members 521 via optical fiber 512. Light source 513 is configured to provide infrared light to at least a portion of the flexible members 521 via optical fiber 514. If auxiliary unit 590 is included in system 500, optical fiber 592 may carry infrared imaging light from light source 591 to at least a portion of the flexible members 521 and optical fiber 594 may carry infrared light from light source 593. Light source 511 may be configured to emit "lambda-one" infrared light and light source 513 may be configured to emit "lambda-two" light that is used as a reference beam or to illuminate a display pixel array (e.g. 113). If auxiliary unit 590 is included in system 500, light source 591 may be configured to emit "lambda-one" infrared light and light source 593 may be configured to emit "lambda-two" infrared light.

Optical fibers 512 or 592 may provide infrared light to an optional emission aperture (not illustrated) included in member structure 510 such that the emission aperture acts as an infrared illuminator that illuminates tissue with an infrared imaging signal 552 carried by optical fiber 512 or 592.

Figure 5C:
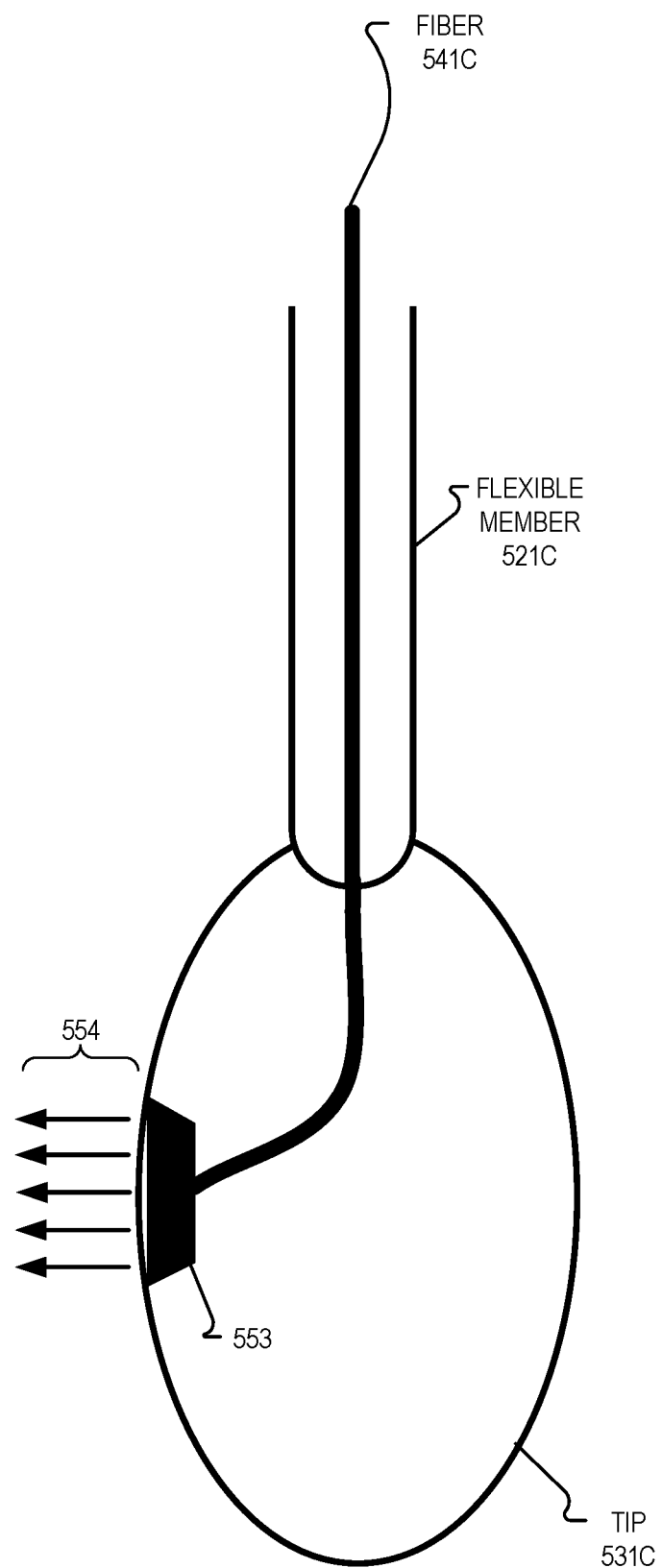

FIG. 5C illustrates a zoomed-in diagram of a lower portion of an example flexible member 521C and its corresponding tip 531C, in accordance with an embodiment of the disclosure. In FIG. 5C, flexible member 521C is hollow so that optical fiber 541C can travel through the hollow portion of flexible member 521C to provide light to aperture 553. Infrared light from light source 511 or 591 may be coupled into fiber 541C, for example. Aperture 553 may function as an infrared illuminator that illuminates tissue with an infrared imaging signal 554. System 500 may include multiple flexible members 521 having tips 531 that include optical fibers 541 providing infrared light to apertures 553 to illuminate tissue with infrared imaging signals 554. A laser diode or an infrared LED may be included in a tip 531 to function as an infrared illuminator, in some embodiments. Having more than one infrared illuminator in different positions may increase the accuracy or spatial coverage of an imaging system.

Figure 5D:
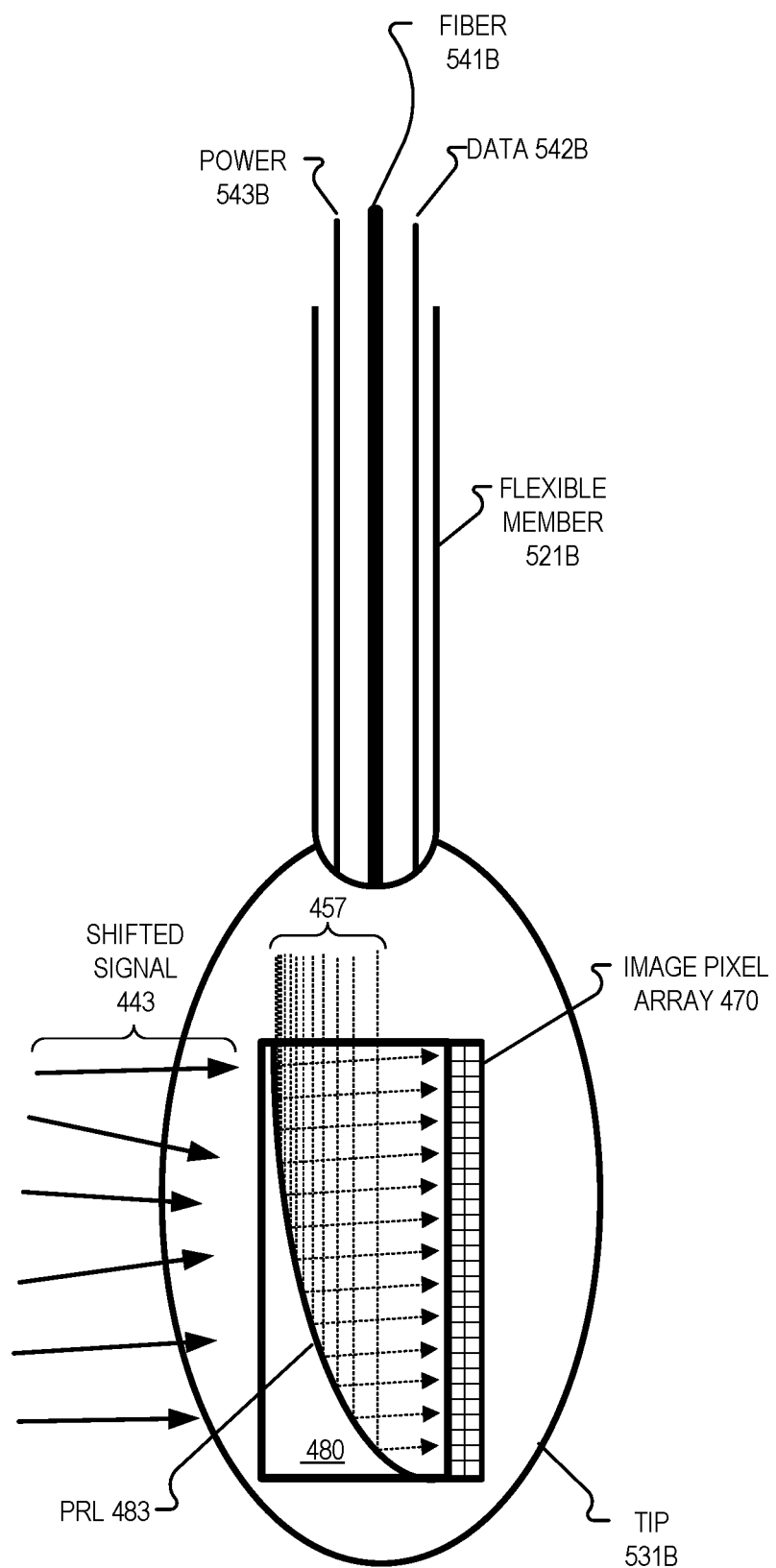

FIG. 5D illustrates a zoomed-in diagram of a lower portion of an example flexible member 521B and its corresponding tip 531B that includes a component of an imaging system. In the illustrated embodiment of FIG. 5D, tip 531B includes an image sensor including image pixel array 470 and optical structure 480 for facilitating the interference of reference beam 457 with a wavelength-shifted signal such as wavelength-shifted exit signal 443. In FIG. 5D, reference beam 457 may be provided to tip 531B by optical fiber 541B running through flexible member 521B. The reference beam 457 may be "lambda-two" light. Power lines 543B may also be provided to tip 531B through flexible member 521B to power electronics in tip 531B, such as image pixel array 470. Data lines 542B may be provided to tip 531B through flexible member 521B so that the image sensor can send and receive data. Data lines 542B may also carry an image capture signal from processing logic 519 to the image sensor that includes image pixel array 470.

Although not specifically illustrated, tips 531 may include other imaging components described in this disclosure, including the imaging components of system 100 and 200. Each imaging component (e.g. display pixel arrays, image pixel arrays, light sources, light sensors, ultrasonic emitters) may be provided power, data, and/or light via wires or optical fiber running through the flexible member 521 associated with the tip 531.

System 500 may include more than one image sensor in more than one tip 531. In FIG. 5A, for example, tip 531A may include an image sensor and tip 531B may include a second image sensor. Each image sensor may receive an infrared reference beam from an optical fiber (e.g. optical fiber 541) running through the flexible members 521A and 521B, respectively. Each optical fiber that delivers an infrared reference beam may receive the infrared reference beam from the same source (e.g. 513 or 593) via a splitter in the optical fiber.

In some embodiments, system 500 may include more than one display pixel arrays in more than one tip 531. In FIG. 5A, for example, tip 531A may include a first display pixel array and tip 531D may include a second display pixel array. Each display pixel array may receive an infrared reference beam from an optical fiber (e.g. optical fiber 541) running through the flexible members 521A and 521D, respectively. Each optical fiber that delivers an infrared reference beam may receive the infrared reference beam from the same source (e.g. 513 or 593) via a splitter in the optical fiber. The infrared reference beam may illuminate the display pixel arrays to generate time-reversed signals, for example.

Figure 6:
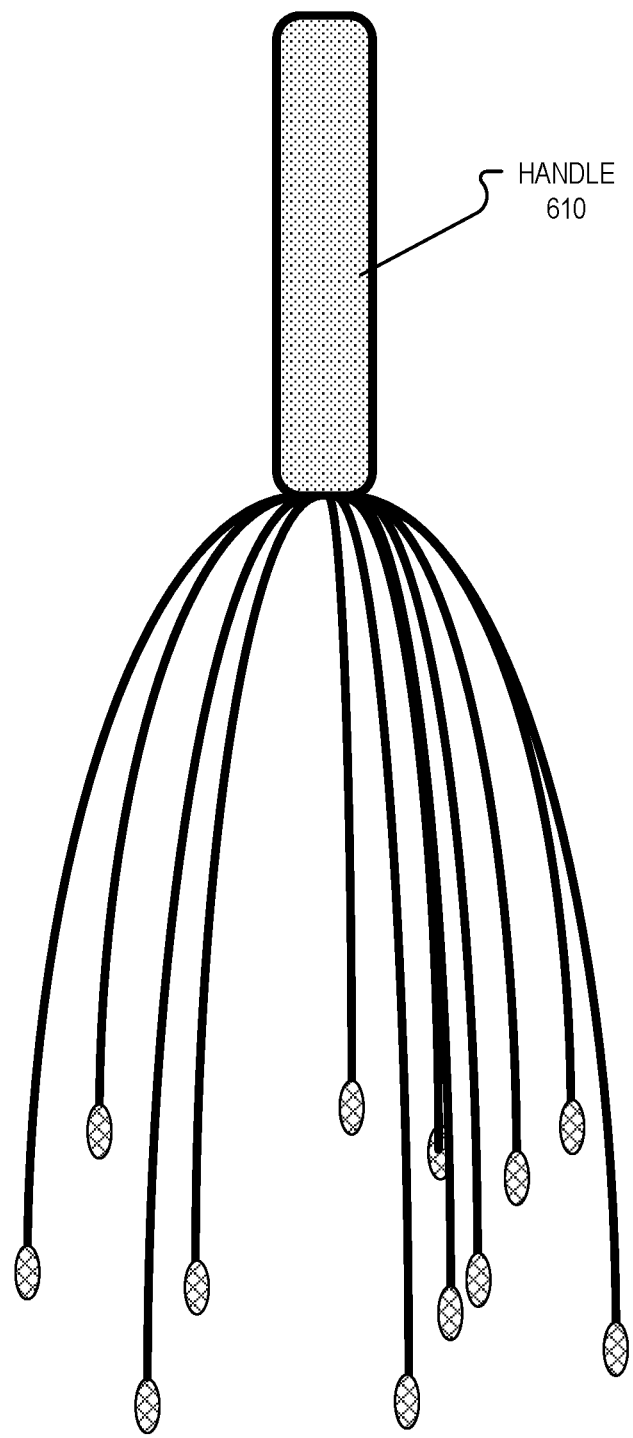
FIG. 6 illustrates an imaging system with an upright handle form factor, in accordance with an embodiment of the disclosure.

FIG. 6 illustrates an example system 600 that has a handle form factor, in accordance with an embodiment of the disclosure. System 600 may have the same features as system 500 except that upright handle 610 replaces the more flush member structure 510. A form factor with upright handle 610 may lend itself to an imaging context where a technician holds the handle to place system 600 in the correct location for imaging. The lower-profile member structure 510 may be utilized in a context where system 500 is worn by a user. The lower-profile member structure 510 may be more easily incorporated into a hat, garment, or wrap, for example to secure the imaging system into place. Some embodiments of the system may be optimized for imaging heads. Some embodiment may be optimized for imaging hands or feet. Some embodiment may be optimized for limbs. Some embodiments may be optimized for imaging a torso area of the body. The shape of member structure 510 and the length and orientation of flexible members 521 may be adjusted to optimize the system for a particular application.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

Communication channels described in this disclosure may include wired or wireless communications utilizing IEEE 802.11 protocols, BlueTooth, SPI (Serial Peripheral Interface), I$^2$C (Inter-Integrated Circuit), USB (Universal Serial Port), CAN (Controller Area Network), cellular data protocols (e.g. 3G, 4G, LTE, 5G), or otherwise The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An imaging device comprising:
a member structure including an ultrasonic emitter configured to emit an ultrasonic imaging signal into tissue;
a plurality of flexible members, wherein the plurality of flexible members have respective first ends coupled to the member structure and have respective second ends; and
a plurality of tips disposed at the respective second ends of the flexible members and configured to contact the tissue,
wherein at least one tip of the plurality of tips includes an image sensor configured to receive an infrared exit signal from the tissue, and
wherein the flexible members have varied lengths, from their respective first ends to their respective second ends, to provide different imaging coverage by the plurality of tips that contact the tissue.

2. The imaging device of claim 1 further comprising:
an infrared illuminator configured to illuminate the tissue with an infrared imaging signal, wherein the infrared exit signal is a wavelength-shifted portion of the infrared imaging signal.

3. The imaging device of claim 2, wherein the infrared illuminator includes an infrared laser.

4. The imaging device of claim 2, wherein the infrared imaging signal is delivered to the tissue through an aperture included in at least one tip in the plurality of tips.

5. The imaging device of claim 4, wherein the infrared imaging signal is received by the aperture by a first optical fiber running through a first flexible member in the plurality of flexible members.

6. The imaging device of claim 2, wherein the infrared illuminator is included in at least one of the tips.

7. The imaging device of claim 1, further comprising an encapsulant material that encapsulates electronics and optical structures of each of the plurality of tips, wherein the encapsulant material is made from a refractive material.

8. The imaging device of claim 1, wherein the image sensor is a first image sensor included in a first tip in the plurality of tips, wherein a second image sensor is included in a second tip in the plurality of tips, and wherein the first image sensor receives an infrared reference beam from a first optical fiber running through a first flexible member in the plurality of flexible members, and wherein the second image sensor receives the infrared reference beam from a second optical fiber running through a second flexible member in the plurality of flexible members.

9. The imaging device of claim 1, wherein the plurality of flexible members are curved inward and positions of the tips expand outward when the plurality of flexible members deflect as tissue is placed between the tips and as the tissue exerts outward pressure on the tips.

10. The imaging device of claim 1, wherein the plurality of flexible members includes power leads to power the image sensor, and wherein the plurality of flexible members includes data lines to initiate image captures with the image sensor and to receive images captured by the image sensor.

11. The imaging device of claim 10, wherein at least a portion of the plurality of flexible members are hollow to run the power leads, the data lines, or optical fibers.

12. The imaging device of claim 1, wherein a display pixel array is included in a tip in the plurality of tips, and wherein the display pixel array receives an infrared reference beam from a first optical fiber running through a first flexible member in the plurality of flexible members, the infrared reference beam illuminating the display pixel array.

13. The imaging device of claim 1, wherein the ultrasonic emitter is configured to emit the ultrasonic imaging signal on a first side of the member structure, and wherein the respective first ends of the plurality of flexible members are coupled to the first side of the member structure.

14. The imaging device of claim 1 further comprising:
processing logic coupled to the ultrasonic emitter to initiate emitting the ultrasonic imaging signal, wherein the processing logic is also coupled to the image sensor to initiate an image capture.

15. The imaging device of claim 14, wherein the processing logic is coupled to receive an interference image captured by the image sensor.

16. An imaging system comprising:
a member structure including an ultrasonic emitter configured to emit an ultrasonic imaging signal;
a plurality of flexible members of varied lengths, wherein the plurality of flexible members have respective first ends coupled to the member structure and have respective second ends;
a plurality of tips disposed at the respective second ends of the flexible members, configured to perform imaging;
an auxiliary unit including a laser light source configured to emit laser light; and
at least one optical fiber coupled between the auxiliary unit and member structure to deliver the laser light to the member structure.

17. The imaging system of claim 16, wherein at least one tip in the plurality of tips receives the laser light.

18. The imaging system of claim 17, wherein the laser light is an infrared reference beam, and wherein the at least one tip includes an image sensor configured to capture an interference pattern of the infrared reference beam interfering with a wavelength-shifted exit signal.

19. The imaging system of claim 18 further comprising:
an infrared illuminator configured to emit an infrared imaging signal, wherein the wavelength-shifted exit signal is a wavelength-shifted portion of the infrared imaging signal.

20. The imaging system of claim 16, wherein the plurality of flexible members are curved inward and positions of the tips expand outward when the plurality of flexible members deflect as tissue is placed between the tips and as the tissue exerts outward pressure on the tips, and wherein the imaging system further comprises at least one of:
a first sensor, located in the member structure, to measure a tension of at least one of the flexible members, wherein a position of a corresponding tip of the at least one of the flexible members is calculated from a tension value generated by the first sensor; and
a second sensor, located in the corresponding tip of the at least one of the flexible members, to generate a force value based on a force exerted on the corresponding tip by the tissue, wherein the position of the corresponding tip is calculated from the force value generated by the second sensor.

* * * * *